US005922596A

United States Patent [19]
Chambon et al.

[11] Patent Number: 5,922,596
[45] Date of Patent: Jul. 13, 1999

[54] PROMOTER OF THE RETINOIC ACID RECEPTOR GENE FOR DIRECTING GENE EXPRESSION

[75] Inventors: Pierre Chambon, Blaesheim, France; Nigel J. Brand, London, United Kingdom; Martin Petkovich, Kingston, Canada

[73] Assignee: Bristol-Myers Squibb Co., New York, N.Y.

[21] Appl. No.: 07/625,334

[22] Filed: Dec. 10, 1990

Related U.S. Application Data

[51] Int. Cl.$^6$ ............... C12N 1/21; C12N 5/10; C12N 15/11; C12N 15/63
[52] U.S. Cl. ............ 435/325; 435/320.1; 435/252.3; 536/24.1
[58] Field of Search .......... 536/27, 24.1; 435/320.1, 435/172.3, 240.1, 240.2, 252.3, 254, 69.1, 325; 935/34

[56] References Cited

U.S. PATENT DOCUMENTS 4,981,784  1/1991  Evans et al. ................ 435/6

FOREIGN PATENT DOCUMENTS

| | | |
|---|---|---|
| 0321362 | 6/1989 | European Pat. Off. . |
| 0325849 | 8/1989 | European Pat. Off. . |
| WO8905355 | 6/1989 | WIPO . |
| WO8905854 | 6/1989 | WIPO . |
| WO8912687 | 12/1989 | WIPO . |
| WO9015815 | 12/1990 | WIPO . |

OTHER PUBLICATIONS

Lotan, R., Biochem. Biophys. Act 605, 33–91 (1980) "Effects of Vitamin A and its Analogs (Retinoids) on Normal and Neoplastic Cells".

Petkovich, M., Brand, N.J., Krust, A. & Chambon, P., Nature 330, 444–450 (1987) "A Human retinoic Acid Receptor which belongs to the family of nuclear receptors".

Giguere, V., Ong, E. S. Segui, P. & Evans, R.M., Nature 330, 624–629 (1987) "Identification of a receptor for the morphogen retinoic acid".

Brand, N., Petkovich, M., Krust, A., Chambon, P., de The, H., Marchio, A., Tiollais, P. & Dejean, A., Nature 332, 850–853 (1988) "Identification of a second human retinoic acid receptor".

Benbrook, D., Lernhardt, E. & Pfahl, M., Nature 333, 669–672 (1988) "A new retinoic acid receptor identified from a hepatocellular carcinoma".

Robertson, M., Nature 330, 420–421 (1987) "Toward a biochemistry of morphogenesis".

Green, S. & Chambon, P., Trends Genet. 4, 309–314 (1988) "Nuclear receptors enhance our understanding of transcription regulation".

Green, S., Issemann, I. & Scheer, E., Nucleic Acids Res. 16, 369 (1988) "A versatile in vivo and in vitro eukaryotic expression vector for protein engineering".

de The, H., Marchio, A., Tiollais, P. and Dejean, A., EMBO J. 8, 429–433 (1989) "Differential expression and ligand regulation of the retinoic acid receptor $\alpha$ and $\beta$ genes".

Maden, M., Ong, D.E., Summerbell, D. and Chytil, F., Nature 335, 733–735 (1988) "Spatial distribution of cellular protein binding to retinoic acid in the chick limb bud".

Boyd, D. et al., J. Endocr. 105, 157–162 (1985) "Nuclear retinoic acid binding protein in human prostate adenomas".

Boyd, D. et al., J. Endocr. 104, p. 48 (1985) "A Soluble Retinoid Binding Protein in Human Hyperplastic Prostate Nuclei".

Cope, F. O. et al., Experientia 40, 276–277 (1984) "Rat testes interstitial cell nuclei exhibit three distinct receptors for retinoic acid".

Rees, J. L. et al., Biochem J. 259, 917–919 (1989) "Differential expression of the $\alpha$ and $\beta$ retinoic acid receptors in tissues of the rat".

Ragsdale, Jr., C. W. et al., Nature 341, 654–657 (1989) "Identification of a novel retinoic acid receptor in regenerative tissues of the newt".

Krust, A. et al., Proc. Natl. Acad. Sci. USA 86, 5310–5314 (1989) "A third human retinoic acid receptor, hRAR–$\gamma$".

Zelent, A., et al., Nature 339, 714–717 (1989) "Cloning of murine 60 and $\beta$ retinoic acid receptors and a novel receptor $\gamma$ predominantly expressed in skin".

Kastner, Ph. et al., Proc. Natl. Acad. Scie. USA 87, 2700–2704 (1990) "Murine isoforms of retinoic acid receptor $\gamma$ with specific patterns of expression".

Brand, N. J. et al., Nucleic Acids Research 18, 6799–6806 (1990) "Characterization of a functional promoter for the human retinoic acid receptor–alpha (hRAR–$\alpha$".

de The, H. et al., Nature 330, 667–670 (1987) "A novel steroid thyroid hormone receptor–related gene inappropriately expressed in human hepato–cellular carcinoma".

de The, H. et al., Nature, 343, 177–180 (1990) "Identification of a retinoic acid responsive element in the retinoic acid receptor $\beta$ gene".

Giguere, V. et al., Mol. Cell. Biol. 10, 2335–2340 (1990) "Identification of a Novel Isoform of the Retinoic Acid Receptor$\gamma$ Expressed in the Mouse Embryo".

Sucov, H. M. et al., Proc. Natl., Acad. Sci USA 87, 5392–5396 (1990) "Characterization of an autoregulated response element in the mouse retinoic acid receptor type $\beta$ gene".

Luckow et al. (1987), Nucleic Acid Research, vol. 15, pp. 5490.

Gunning et al. (1987), Proc. Natl. Acad. Sci, vol 84, pp. 4831–4835.

*Primary Examiner*—Johnny F. Railey, II
*Attorney, Agent, or Firm*—James M. Bogden; Thomas R. Savitsky; Audrey F. Sher

[57] ABSTRACT

An isolated DNA sequence capable of directing gene expression comprising a hRAR-$\alpha$ promoter or a hRAR-$\alpha$ promoter element, expression vectors containing the DNA sequence and host cells containing the expression vectors.

12 Claims, 6 Drawing Sheets

PROMOTER OF THE RETINOIC ACID RECEPTOR GENE FOR DIRECTING GENE EXPRESSION

BACKGROUND OF THE INVENTION

Retinoic acid (RA) plays a major role in a variety of developmental processes [see Strickland, S. et al., Cell 15, 393–403 (1978); Hogan B. L. M. et al., Nature 291, 235–237 (1981); Roberts, A. B. et al., Academic Press 2, 209–286 (1984); Maden, M., Trends in Genetics 1, 103–107 (1985); Brockes, J. P., Neuron 2, 1285–1294 (1989); Eichele, G., Trends in Genetics 5, 246–251 (1989); and Brockes, J., Nature 345, 766–768 (1990) for references and reviews]. In culture, certain murine and human teratocarcinoma cell lines respond to RA by undergoing differentiation forming, for example, cells which resemble primitive endoderm cells or neurons [Strickland, S. et al., Cell 15, 393–403 (1978); Hogan, B. L. M. et al., Nature 291, 235–237 (1981); Andrews, P. W., Developmental Biology 103, 285–293 (1984); Sharma, S. et al., Developmental Biology 125, 246–254 (1988)]. Often, these events are accompanied by specific changes in gene expression (for example, see Wang, S. -Y. et al., Proc. Natl. Acad. Sci. USA 80, 5880–5884 (1983); Marotti, K. R. et al., Developmental Biology 108, 26–31 (1985); LaRosa, G. J. et al., Mol. Cell Biol. 8, 3906–3917 (1988); and Vasios, G. W. et al., Proc. Natl. Acad. Sci. USA 86, 9099–9103 (1989) and references therein). RA has been strongly implicated as an active morphogen in pattern formation, chiefly using the developing chick limb bud and the regenerating urodele amphibian limb blastema as models [Maden, M., Trends in Genetics 1, 103–107 (1985); Brockes, J. P., Neuron 2, 1285–1294 (1989); Eichele, G., Trends in Genetics 5, 246–251 (1989); Brockes, J., Nature 345, 766–768 (1990); Thaller, C. et al., Nature 327, 625–628 (1987); and Slack., J. M. W., Nature 327, 553–554 (1987) and references therein].

The role of RA in controlling such diverse processes has been strengthened by the identification of three related nuclear receptors for RA, termed retinoic acid receptors (RARs) $\alpha$, $\beta$ and $\gamma$, that are members of the steroid/thyroid hormone receptor superfamily of inducible transcriptional enhancer factors (Evans, R. M., Science 240, 889–895 (1988); Green, S. et al., Trends in Genetics 4, 309–314 (1988); Beato, M., Cell 56, 335–344 (1989)], and which bind RA selectively and with high affinity [Petkovich, M. et al., Nature 330, 444–450 (1987); Giguere, V. et al., Nature 330, 624–629 (1987); Brand, N. et al., Nature 332, 850–854 (1988); Benbrook, D. et al., Nature 333, 669–672 (1988); Krust, A. et al., Proc. Natl. Acad. Sci. USA 86, 5310–5314 (1989); Zelent, A. et al., Nature 339, 714–717 (1989)]. The three RAR genes are expressed with varying degrees of tissue specificity during embryonic development and in adult tissues, and are found in a number of cultured cell lines [Krust, A. et al., Proc. Natl. Acad. Sci. USA 86, 5310–5314 (1989); Zelent, A. et al., Nature 339, 714–717 (1989); Dolle, P. et al., Nature 342, 702–705 (1989); Kastner, P. et al., Proc. Natl. Acad. Sci. USA 87, 2700–2704 (1990); Ruberte, E. et al., Development 108, 213–222 (1990)]. Alignment of RAR amino acid sequences and their comparison with other nuclear receptors has allowed the definition of six regions within the protein, termed A–F [Krust, A. et al., Proc. Natl. Acad. Sci. USA 86, 5310–5314 (1989); Zelent, A. et al., Nature 339, 714–717 (1989); Krust, A. et al., EMBO J. 5, 891–897 (1986)], including the two highly conserved regions C and E; corresponding to the DNA binding and the ligand binding domains, respectively. In additon, recent evidence indicates that isoforms of mouse and human RAR-$\gamma$, which differ in the amino-terminal region A and 5' untranslated region (5'-UTR), are generated through alternative splicing [Krust, A. et al., Proc. Natl. Acad. Sci. USA 86, 5310–5314 (1989); Kastner, P. et al., Proc. Natl. Acad. Sci. USA 87, 2700–2704 (1990); Giguere V. et al., Mol. Cell. Biol. 10, 2335–2340 (1990)].

Previously, two partial hRAR-$\alpha$ complementary DNA (cDNA) sequences, which differed in the 5' region, were published by Petkovich, M. et al., Nature 330, 444–450 (1987) and Giguere, V. et al., Nature 330, 624–629 (1987). The hRAR-$\alpha$ cDNA clone of Petkovich et al. was deduced to encode a protein of 432 amino acids, though an upstream in-frame termination codon was not seen [Petkovich, M. et al., Nature 330, 444–450 (1987)]. In contrast, the clone of Giguere, V. et al., Nature 330, 624–629 (1987) encoded a 462 amino acid protein that began at a methionine codon beyond the 5' border of the Petkovich et al. cDNA clone and was preceded by an in-frame TGA termination codon. Neither of the two cDNA clones was full-length in their 5' region. Described here is the isolation and characterization of cDNA and genomic DNA clones containing the sequences encoding the A region and the whole 5'-untranslated region (5'-UTR) of hRAR-$\alpha$. This has led to the determination of the exon-intron organization of the 5' region of hRAR-$\alpha$ gene and to the isolation of a functional promoter which resembles some RNA polymerase B (II) promoters that lack a TATA box [Smale, S. T. et al., Cell 57, 103–113 (1989); Smale, S. T. et al., Proc. Natl. Acad. Sci. USA 87, 4509–4513 (1990)].

SUMMARY OF THE INVENTION

The present invention concerns an isolated DNA sequence capable of directing gene expression comprising a hRAR-$\alpha$ promoter or a hRAR-$\alpha$ promoter element.

The present invention further concerns an expression vector comprising an isolated DNA sequence capable of directing gene expression which comprises a hRAR-$\alpha$ promoter or a hRAR-$\alpha$ promoter element.

The present invention also concerns a host cell containing an expression vector comprising an isolated DNA sequence capable of directing gene expression which comprises a hRAR-$\alpha$ promoter or a hRAR-$\alpha$ promoter element.

DESCRIPTION OF THE DRAWINGS

FIG. 1 (A) shows a schematic representation of hRAR-$\alpha$ genomic clones. A lambda genomic clone $\lambda$91.1, isolated from a human leucocyte genomic DNA library constructed in EMBL 3 with an oligonucleotide ME012 specific for the A region hRAR $\alpha$ [Petkovich, M. et al., Nature 330, 444–450 (1987)], a partially overlapping clone $\lambda$31.1 and plasmid subclones derived from them are shown. Clone pBP31.1 contains exon 2 of hRAR-$\alpha$, comprising the 5'-UTR and region A (hatched box) of the receptor. Clone pRS7 contains exon 1 comprising the rest of the 5'-UTR and 5' flanking sequences. The exons are separated by an intron of at least 12 kb in length. Restriction enzyme sites are: B, Bam HI; E, Eco RI; K, KpnI; P, PstI; S, Sal I; Sm, Sma I. The 5' and 3' borders of the exons (determined by nuclease S1 mapping) are numbered relative to the beginning of exon 1 and their lengths are indicated in parentheses. The position of ME012 and a nuclease S1 probe extended from the oligonucleotide MQ300, together with the lengths of the probe and a fragment protected by it, are indicated.

FIG. 1 (B) shows promoter-reporter constructs for testing the function of the hRAR-$\alpha$ promoter. The positions and lengths of end-labelled probes used in nuclease S1 mapping are indicated, as are the lengths of the S1 nuclease protected products. hRAR-α promoter constructs, which contain a 614 bp Bam HI-Sma I fragment comprising hRAR-α sequences from −509 to +105 [SEQ. ID NO. 1], are described elsewhere in the application. The globin reporter constructs are based on the vector pAK4 and contain rabbit β-globin sequences from −9. The reporter pG1B contains the SV40 72 bp enhancer linked 5' to te β-globin promoter and coding sequences from −109 [Wasylyk, C. et al., EMBO J. 5, 553–560 (1986)]. The CAT reporters are based on the promoterless vector pBLCAT3+ [Luckow, B. et al., Nucleic Acids Res. 15, 5490 (1987)].

FIG. 2 (A–B) shows the nucleotide sequence of the human RAR-α promoter, exons 1 and 2 (upper case), and immediate flanking intronic regions (lower case), derived from genomic subclones PBP31.1, pRS7 and a cDNA clone T2/20. The nucleotide sequence for exon 1 and its immediate flanking intronic region is SEQ.ID.NO.:1 and the nucleotide sequence for exon 2 and its immediate flanking intronic region is SEQ.ID.NO.:2. The sequence of part of exon 3 (SEQ. ID. NO.:3), determined from T2/20, is also shown, starting at the polylinker Eco RI site for this clone (underlined) and the limits of the cDNA sequence are denoted by brackets. Other restriction sites, shown in FIG. 1A, are underlined. P▲ and ᴬG represent the 5' limits of hRAR-α cDNA sequences published previously by Petkovich, M. et al., Nature 330, 444–450 (1987) and Giguere, V. et al., Nature 330, 624–629 (1987), respectively. The nucleotide sequence is numbered relative to +1, the most 5' of three transcription start-sites, P1–3, determined by nuclease S1 mapping [Zenke, M. et al., EMBO J. 5, 387–397 (1986)]. The sequences and orientation of oligonucleotides MQ9, MQ300 and ME012, used as probes or for generating probes for nuclease S1 mapping analysis, are denoted by a broken underline. The amino acid sequence of region A (SEQ. ID. NO.:8) and part of region B (SEQ. ID. NO.:9) of hRAR-α is shown and numbered relative to the first ATG. The "Kozak" sequence [Kozak, M., J. Cell Biol. 108, 229–241 (1989)] surrounding this ATG is underlined. A termination codon TGA upstream of and in frame with the ATG is underlined. Four short open reading frames (sORF), shown with their predicted amino acid sequences, are numbered according to proximity to the 5' end, and their possible Kozak sequences are underlined. The first predicted amino acid sequence, sORF 1, is SEQ.ID.NO.:4; the second predicted amino acid sequence, sORF 2, is SEQ.ID.NO.:5; the third predicted amino acid sequence, sORF 3, is SEQ.ID.NO.:6; and the fourth predicted amino acid sequence, sORF 4, is SEQ.ID.NO.:7. Possible binding sites for the transcription factor Sp1, based on a consensus 5'-$_T^G$GGGCGG$_{AAT}^{GGC}$-3' (SEQ. ID. NO.:10) [Pynan, W. S. et al., Nature 319, 246–248 (1986)], are boxed and their orientation indicated by arrows. A sequence 5'-GCGGGGGCGG-3' (SEQ.ID. NO.:11) identical to a binding site for Krox-20 [Chavrier, P. et al., EMBO J 9, 1209–1218 (1990)] at −120/−111, is indicated by a broken overline. The sequence 5'-AGGTGTGGGTG-3' SEQ. ID. NO.:12) at −347/−337, which resembles the SV40 enhancer GT-I motif [Davidson, I. et al., Cell 54, 931–942 (1988)], is denoted by a solid underline. Two copies of a sequence 5'-GGTCA-3' SEQ. ID. NO:13) beginning at −485 and −479 are also underlined. Finally, two sequences resembling elements which, in the Adenovirus E4 promoter, bind a factor E4TF1 [Jones, N. C. et al., Genes & Development 2, 267–281 (1988)] are shown by solid overlines, orientation denoted by arrows. Other symbols are described herein below.

FIG. 3 shows the determination of hRAR-α transcription start-sites by nuclease S1 mapping. A BamH I-Sma I fragment from the genomic subclone pRS7 containing the promoter region for human RAR-α was cloned upstream of rabbit β-globin sequences in the expression vector pAL4. HeLa cells were transfected with recombinant plasmids (FIG. 1B) containing either the hRAR-α promoter fragment inserted in the natural (pAL4BS, lane 1) or reverse orientation (pAL4SB, lane 2), or the promoterless parent vector, pAL4 (lane 3). An internal reference β-globin plasmid, pG1B [Wasylyk, C. et al., EMBO J. 5, 553–560 (1986)], was co-transfected in all cases to normalize for expression from the pAL constructs. Cytoplasmic RNA was prepared subsequently and analyzed by nuclease S1 mapping. Gels were exposed to Kodak-AR film at −80° C. for up to 10 days to visualize the hRAR-α-specific protected fragments. Transcripts identified by nuclease S1 mapping that originate within the hRAR-α promoter are labelled by arrows (P1, P2 and P3, lane 1) and their sizes shown. An S1 nuclease protected fragment of 69 nt from pG1B seen in all samples is indicated. A dideoxy sequencing ladder, primed with the p-globin-specific oligonucleotide M6 used to generate the S1 probe, is shown alongside. Pr corresponds to undigested probe.

FIG. 4 (A–D) shows the activity of hRAR-α promoter-driven CAT reporter genes in cultured cells.

(A) HeLa cells were transfected with the indicated amount of either the recombinant pRARA12 (FIG. 1B) (lanes 1–4) containing the hRAR-α promoter linked to the E. coli CAT gene or the promoterless parent vector pBLCAT3+ [Luckow, B. et al., Nucleic Acids Res. 15, 5490 (1987)] (lanes 5–8), 2 µg of the β-galactosidase indicator plasmid pCH110 (Pharmacia) and carrier DNA (BSM+) to a final level of 20 µg. Transfection, cell culture and assays for CAT activity were performed as detailed herein below. Transfection efficiency was normalized by measuring the amount of β-gal activity in ⅕ of the extract prepared from one 90 mm dish of transfected cells as described herein below. The equivalent of 30 units of β-gal activity for each extract were assayed for CAT activity.

(B) Graphic representation of the data from (A). The percentage of chloramphenicol acetylated, calculated by cutting out the regions corresponding to acetylated and non-acetylated forms of $^{14}$C-chloramphenicol and scintillation counting, is plotted against the amount (in µg) of pRARA12 (solid circles) or pBLCAT3+ (open circles) transfected.

(C) HeLa cells were transfected with either 2 µg of pRARA12 (lanes 1 and 2, 5 and 6, 9 and 10) or 2 µg pBLCAT3+ (lanes 3 and 4, 7 and 8, 11 and 12), together with either the wild-type RAR-α expression vector RAR-αφ [Brand, N. et al., Natures 332, 850–854 (1988)] (lanes 5–8), the wild-type RAR-β expression vector RAR-βφ [Brand, N. et al., Nature 332, 850–854 (1988)] (lanes 9–12) or the parental expression vector pSG1 [obtained from Stephen Green; see, Green, S. et al., Nucleic Acids Research 86, 69–83 (1988)] (lanes 1–4). The β-gal expression vector pCH110 and BSM were co-transfected as described in Brand et al., supra. and the equivalent of 50 β-gal units were assayed in each case. As a RA trans-activation control, HeLa cells were co-transfected with 100 ng of RAR-β-ER.CAS [Brand, N. et al., supra.] and 1 µg of the reporter vit-tk-CAT (lanes 13 and 14); 10 β-gal units from each transfection were assayed. Transfections were done in duplicate and one of each pair was treated with $10^{-7}$M RA (odd numbers) or vehicle alone (even numbers), as described herein below. The results shown represent a typical experiment.

(D) Expression from the hRAR-α promoter in the mouse EC cell line P19.6.4 µg of either pRARA12 (lane 1) or pBLCAT3+ (lane 2) were transfected with pCH110 and BSM to 20 µg. 1 µg of the SV40-driven CAT reporter pSVCAT was also transfected (lane 3). 50 β-gal units were assayed in each case.

DETAILED DESCRIPTION OF THE INVENTION

The present invention concerns compositions and methods for regulating gene expression. In particular, promoters and promoter elements which are capable of directing gene expression are disclosed. More particularly, the present invention concerns an isolated DNA sequence capable of directing gene expression comprising a hRAR-α promoter or a hRAR-α promoter element.

Figure 2A:
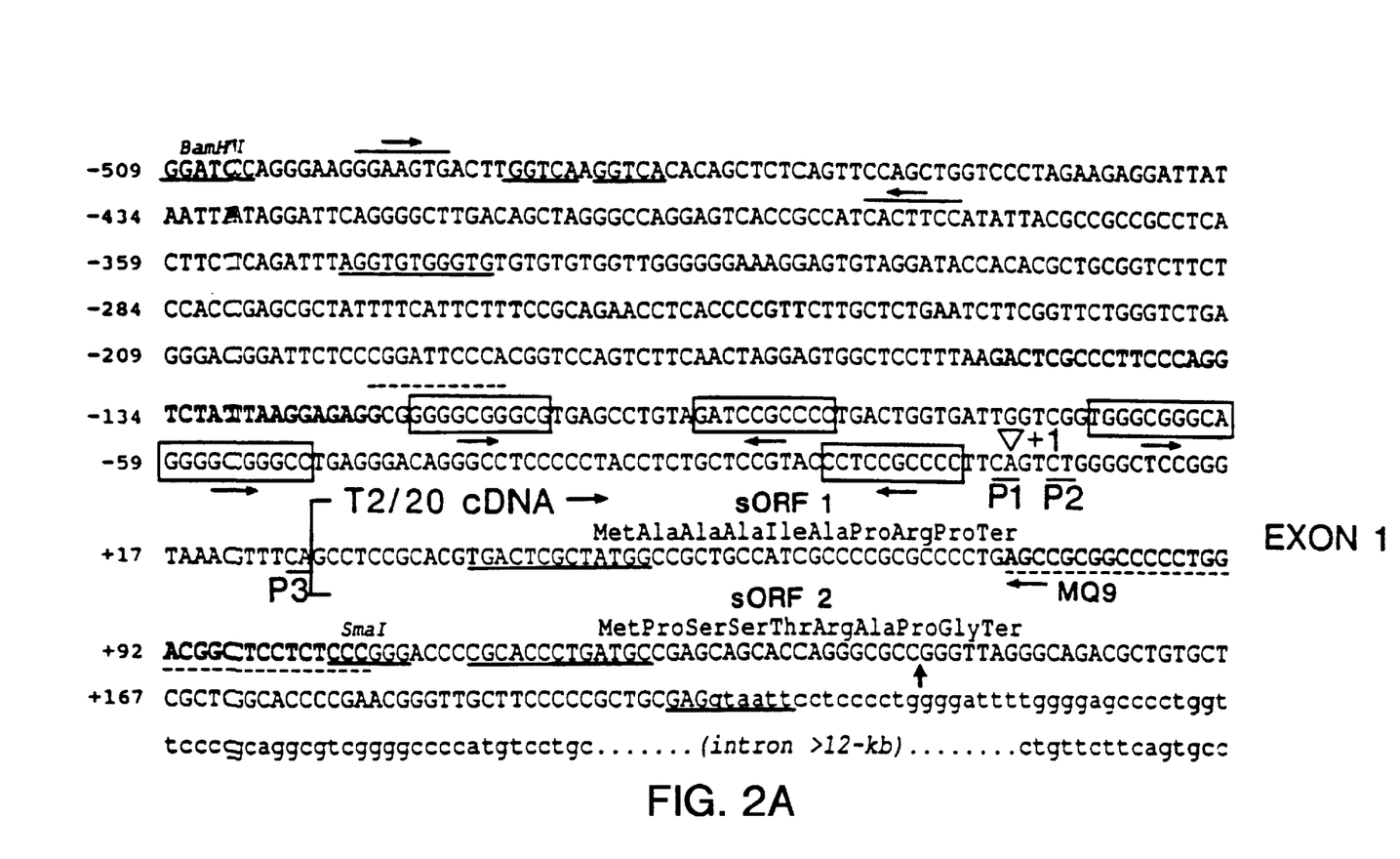
Figure 2B:
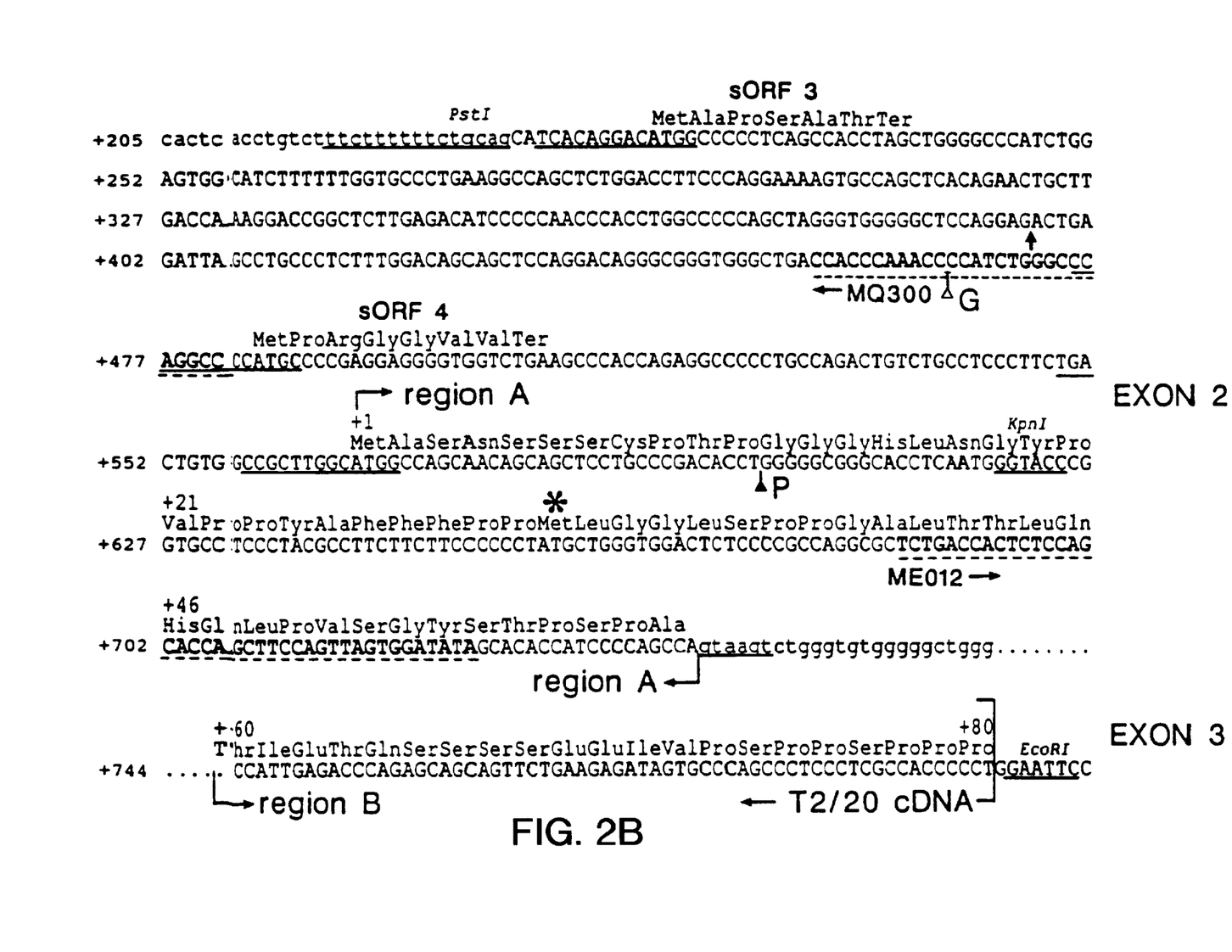

The promoter region of the present invention comprises the promoter region of the hRARα gene. This hRARα promoter region has been cloned and sequenced and corresponds to nucleotides −509 to +105 of SEQ. ID. NO.:1 as shown in FIG. 2.

The present invention encompasses the entire hRAR-α promoter region as well as particular sequences (elements) of the hRARα promoter region. These promoter elements are capable of directing gene transcription, and therefore ultimately gene expression, and can be used with other portions of the hRARα promoter or alternatively with heterologous promoters or heterologous promoter elements to control gene transcription.

The DNA sequences of the present invention comprising a hRAR-α promoter or a hRAR-α promoter element can be obtained using various methods known in the art. At least three alternative principal methods may be employed:

(1) the isolation of the DNA sequence from genomic DNA which contains the sequence;

(2) the chemical synthesis of the DNA sequence; and (3) the synthesis of the DNA sequence by polymerase chain reaction (PCR).

In the first approach, a human genomic DNA library can be screened in order to identify a DNA sequence comprising a hRAR-α promoter or hRAR-α promoter element.

In the second approach, a DNA sequence comprising a hRAR-α promoter or a hRAR-α promoter element can be chemically synthesized. For example, a DNA sequence comprising a hRAR-α promoter or a hRAR-α promoter element can be synthesized as a series of 100 base oligonucleotides that can then be sequentially ligated (via appropriate terminal restriction sites) so as to form the correct linear sequence of nucleotides.

In the third approach, a DNA sequence comprising a hRAR-α promoter or a hRAR-α promoter element can be synthesized using PCR. Briefly, pairs of synthetic DNA oligonucleotides at least 15 bases in length (PCR primers) that hybridize to opposite strands of the target DNA sequence can be used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the 5' ends of the PCR primers. See, U.S. Pat. Nos. 4,683,195 and 4,683,202.

While the nucleotide sequence of the promoter (including the promoter elements) are shown in FIG. 2 (nucleotides −509 to +105; SEQ. ID. NO. 1) and reference is made to such sequence in the specification, it is recognized that nucleotide modifications can be made which do not affect the promoter or promoter element function. These modified nucleotide sequences may be prepared, for example, by mutating the nucleotide sequence so that the mutation results in the deletion, substitution insertion, inversion or addition of one or more nucleotides using various methods known in the art. For example, the methods of site-directed mutagenesis described in Taylor, J. W. et al., Nucl. Acids Res. 13, 8749–8764 (1985) and Kunkel, J. A., Proc. Natl. Acad. Sci. USA 82, 482–492 (1985) may be employed. In addition, kits for site-directed mutagenesis may be purchased from commercial vendors. For example, a kit for performing site-directed mutagenesis may be purchased from Amersham Corp. (Arlington Heights, Ill.). The present invention encompasses all such modified nucleotide sequences.

The nucleotide sequence comprising the promoter region or elements thereof can be operably linked to the coding region of any gene of interest to express that gene in an appropriate host cell. By operably linked is intended operably linked for promoter and elements. For expression of a gene of interest, it is preferred that the entire hRAR promoter region (nucleotides −509 to +105 of SEQ. ID. NO.:1 as shown in FIG. 2) be operably linked to the gene of interest. As shown below in the example section, the hRAR-α promoter is capable of directing the expression of heterologous genes; the expression of homologous genes is also contemplated.

An "operably linked" hRARα promoter or promoter element will direct the transcription of a nucleic acid molecule joined in proper reading frame. With regard to heterologous promoters, the promoters and elements of the invention are operably linked when they control the function of such heterologous promoters.

As noted above, the hRAR-α promoters and promoter elements of the present invention can be utilized to express any gene of interest. Typically, an expression vector is used for this purpose. Thus, the present invention further concerns expression vectors comprising an isolated DNA sequence capable of directing gene expression which comprises a hRAR-α promoter or a hRAR-α promoter element. The expression vectors preferably contain a hRAR-α promoter having a nucleotide sequence corresponding to nucleotides −509 to +105 as shown in FIG. 2. Also preferred are expression vectors further comprising a homologous or heterologous gene operatively linked to the hRAR-α promoter or the hRAR-α promoter element.

Expression vectors of utility in the present invention are often in the form of "plasmids", which refer to circular double stranded DNAs which, in their vector form, are not bound to the chromosome. However, the invention is intended to include such other forms of expression vectors which serve equivalent functions and which become known in the art subsequently hereto.

Expression vectors useful in the present invention typically contain an origin of replication, a hRAR-α promoter or a hRAR-α promoter element located in front of (i.e., upstream of) the gene of interest, transcription termination sequences and the remaining vector. The expression vectors can also include other DNA sequences known in the art, for example, stability leader sequences which provide for stability of the expression product, secretory leader sequences which provide for secretion of the expression product, sequences which allow expression of the structural gene to be modulated (e.g., by the presence or absence of nutrients or other inducers in the growth medium), marking sequences which are capable of providing phenotypic selection in transformed host cells, and sequences which provide sites for cleavage by restriction endonucleases. The characteristics of the actual expression vector used must be compatible with the host cell which is to be employed. An expression vector as contemplated by the present invention is at least capable of directing the transcription, and preferably the expression, of the gene of interest. DNA sequences of the present invention. Suitable origins of replication include, for example, that of the Simian virus 40 (SV40). Suitable termination sequences include, for example, that of the Simian virus 40 (SV40). Virtually any gene of interest, for example, genes coding for *Escherichia coli* chloramphenicol acetyl transferase (CAT) and therapeutic products such as interferon, may be employed. All of these materials are known in the art and many are commercially available.

Suitable expression vectors containing the desired coding and control sequences may be constructed using standard recombinant DNA techniques known in the art, many of which are described in Sambrook, et al., *Molecular Cloning: A Laboratory Manual,* 2nd edition, Cold Spring Harbor Laboratory, Cold Spring Harbor, N.Y. (1989).

The present invention additionally concerns host cells containing an expression vector comprising an isolated DNA sequence capable of directing gene expresion which comprises a hRAR-α promoter or a hRAR-α promoter element. Preferably, the hRAR-α promoter has the nucleotide sequence corresponding to nucleotides −509 to +105 of SEQ. ID. NO.:1 as shown in FIG. 2. Also preferred are host cells containing an expression vector further comprising a homologous or heterologous gene operatively linked to the hRAR-α promoter or the hRAR-α promoter element. Suitable host cells include, for example, human HeLa cells or African Green Monkey cells CV-1 and COS-1.

Preferred as host cells are HeLa and COS-1 cells.

Expression vectors may be introduced into host cells by various methods known in the art. For example, transfection of host cells with expression vectors can be carried out by the calcium phosphate precipitation method. However, other methods for introducing expression vectors into host cells, for example, electroporation, biolistic fusion, liposomal fusion, nuclear injection and viral or phage infection can also be employed.

Once an expression vector has been introduced into an appropriate host cell, the host cell can be cultured under conditions permitting expression of large amounts of the polypeptide encoded by the gene of interest.

Host cells containing an expression vector which contains a DNA sequence coding for a gene of interest may be identified using various methods known in the art. For example, DNA-DNA hybridization, assessing the presence or absence of marker gene functions, assessing the level of transcription as measured by the production of mRNA transcripts of the gene of interest in the host cell, and detecting the gene product immunologically can be employed.

The DNA sequences of expression vectors, plasmids or DNA molecules of the present invention may be determined by various methods known in the art. For example, the dideoxy chain termination method as described in Sanger et al., Proc. Natl. Acad. Sci. USA 74, 5463–5467 (1977), or the Maxam-Gilbert method as described in Proc. Natl. Acad. Sci. USA 74, 560–564 (1977) may be employed.

It should be understood specific nucleotides or regions within the promoter or promoter elements may be identified as necessary for regulation. These regions or nucleotides may be located by fine structural dissection of the elements, and can be studied by experiments which analyze the functional capacity of promoter mutants. For example, single base pair mutations of promoter elements can be generated utilizing PCR. Oligonucleotides can then be designed that code for the regions of interest, except that single base pair changes will be made in the region that is under examination. In this fashion, a number of mutated promoter regions are amplified, and then cloned back into reporter constructs and evaluated with transfection and CAT assay techniques (as set forth in the example section below). These amplified fragments can be cloned back into the context of the hRAR-α promoter and also into the heterologous promoter constructs. In this fashion, the exact nucleotide sequences that are important in directing gene transcription are identified.

This analysis will also identify nucleotide changes which do not effect promoter function, or which may increase promoter function. Thus, functional derivative promoters and promoter elements can also be constructed.

Functional analysis of the promoter region can be facilitated by footprint and gel-shift studies. Knowledge of the exact base pairs important in mediating binding of proteins provides evidence of bases important in mediating the transcriptional response.

The invention therefore further encompasses the base pairs important in DNA-protein interaction. Such base pairs can be elucidated. Genomic fragments containing the areas of interest can be employed in in vitro footprinting experiments [Galas et al., Nucleic Acids Res. 9, 6505–6525 (1981)]. Isolated restriction fragment can be radiolabled and subsequently incubated with nuclear extracts made with established techniques from cells expected to contain DNA binding proteins which will bind to the fragment [for example, Dignam et al., Nucleic Acids Res. 11, 1475–1489 (1983)]. Labeled DNA fragments are incubated with the nuclear extracts, digested with DNAse I, and electrophoresed on a denaturing polyacrylamide gel. DNA binding proteins in the cell extract bind to their recognition sequence contained in the labeled restriction fragment, and protect the DNA from digestion by the DNAse. Regions of protection delineate the binding site. Maxam and Gilbert sequencing reactions of the fragment can be used as a marker to define the nucleotides protected from DNAse digestion.

The invention is further drawn to the identification and characterization of trans-acting factors which interact with the promoter or promoter elements. Cis-acting regulatory sequences serve as binding sites for proteins which are termed transacting factors (TAF) [Dynan W. S., Tjian T. Nature 316, 774–778 (1985); Maniatis, T. et al., Science 236, 1237–1245 (1987)]. Each gene is presumed to bind one or more proteins at each of its regulatory sequences, and these proteins interact with one another and RNA polymerase II in a fashion that controls transcription.

TAFs have been identified in nuclear extracts by their ability to bind to and retard electrophoretic mobility of cis-acting sequence DNA fragments [Dignam, J. D. et al., Nucleic Acids Res. 11, 1475–1489 (1983); Dynan, W., Cell 58, 1–4 (1989); Fletcher, C. et al., Cell 773–781 (1987); Scheidereit, C. et al., Cell 51, 783–793 (1987)].

The cis-acting sequences are useful in gel retardation assays to determine binding activity in nuclear extracts. The technology for gel shift assays is described in the literature and includes many of the same reagents used in footprint experiments [Fried, M. et al., Nucleic Acids Res. 9, 6505–6525 (1981); Revzin, A., Biotechniques 7, 346–355 (1989); Strauss, F. A. et al., Cell 37, 889–901 (1984)]. Either $^{32}$P-labeled restriction fragments or annealed pairs of complementary oligos are incubated with nuclear extracts and poly d(I-C) in a binding buffer, and the products of this reaction electrophoresed on a non-denaturing polyacrylamide gel. The location of the DNA fragment on the gel as determined with autoradiography is retarded in cases where protein has bound to the DNA. The extend of the retardation is a relative function of the size of the protein.

The binding proteins so identified can then be purified and ultimately cloned using known techniques.

The promoters and promoter elements also find use in transgenic studies. Transgenic mice provide a powerful genetic model for the study of a number of human diseases including cancer. They have also provided an important in vivo method for studies of gene regulation that have confirmed and extended observations made with transfection reporter gene experiments [Palmiter, F. L. et al., Ann. Rev. Genet. 20, 465–499 (1986)]. Studies aimed at dissecting the signals allowing developmental relation of gene expression can rarely be performed in cell culture models and is probably best studied with a transgenic model. This type of experiment is possible because of the remarkable conservation between species of regulatory sequences, such that human regulatory signals are accurately interpreted by the mouse transcription machinery.

Constructs expressed in transgenic mice could therefore provide much information about the regulation of the hRARα gene.

Transgenic mice can be made by methods known in the art. The most widely used method through which transgenic animals have been produced involve injecting a DNA molecule into the male pronucleus of a fertilized egg [Brinster et al., Cell 27, 223 (1981); Costantini et al., Nature 294, 982 (1981); Harpers et al., Nature 293, 540 (1981); Wagner et al., Proc. Natl. Acad. Sci. USA 78, 5016 (1981); Gordon et al., Proc. Natl. Acad. Sci. USA 73, 1260 (1976)].

Once the DNA molecule has been injected into the fertilized egg cell, the cell is implanted into the uterus of recipient female and allowed to develop into an animal. Thus, all of the cells of the resulting animal should contain the introduced gene sequence.

The resulting transgenic mice or founders can be bred and the offspring analyzed to establish lines from the founders that express the transgene. In the transgenic animals, multiple tissues can be screened to observe for gene expression. RNA studies in the various transgenic mouse lines will allow evaluation of independence of the integration site to expression levels of the transgene. See, Hogan, B. et al., *Manipulating the mouse embryo: a laboratory manual,* Cold Spring Harbor Press, Cold Spring Harbor, N.Y. (1986).

The hRAR-α promoter and promoter elements may also provide a useful means for carrying out gene therapy. For the most part, constructs comprising the promoter or promoter elements will be utilized to target gene expression in those cells when the hRAR-α gene is normally expressed. Any means available in the art for transfer of the constructs into animals, including humans, can be utilize. This includes viral vectors, particularly retroviral vectors (see, for example, Zweibel et al, Science 243, 220 (1989), and the references cited therein), as well as other methods.

The following examples are further illustrative of the present invention. These examples are not intended to limit the scope of the present invention, and provide further understanding of the invention.

EXAMPLE 1

Isolation of genomic and cDNA encoding the hRAR-α 5' region

Figure 1A:
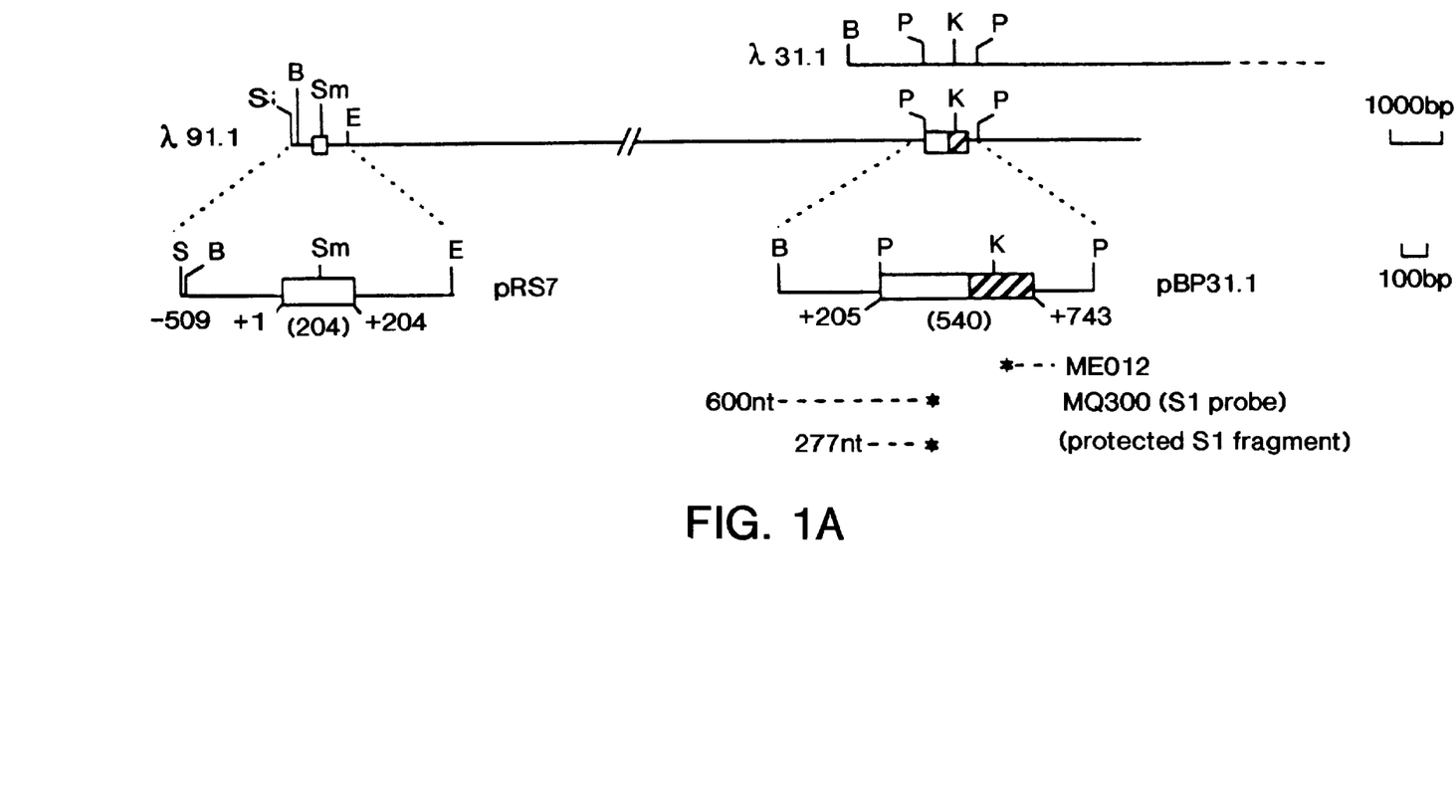

To isolate genomic sequences encoding the hRAR-α gene 5' region, a human leucocyte genomic DNA library constructed in the lambda vector EMBL3 was screened using an oligonucleotide, MEO12, specific for the A region of hRAR-α (see FIGS. 1A and 2). This region exhibits no homology with either hRAR-β [Brand, N. et al., Nature 332, 850–854 (1988)] or hRAR-γ [Krust, A. et al., Proc. Natl. Acad. Sci. USA 86, 5310–5314 (1989)]. This library was constructed from Sau3A fragments (partial digest) of human leucocyte DNA cloned into the Bam HI site of the vector EMBL3, supplied by Transgene S. A. (Strasbourg, France). Approximately 400,000 plaques were plated on a lawn of *Escherichia coli* $Q_{358}$ on 150 mm diameter plates. Duplicate nylon filters (Biodyne) were laid on the plates and phage DNA was bonded to the filters according to the manufacturer's instructions. Filters were hybridized as described in Petkovich et al., supra, except that hybridization was carried out at 50° C. for 36 hours using a [$^{32}$P]-end labelled oligonucleotide MEO12 part of SEQ.ID.NO.:2, see FIG. 2) from the 5' end of the hRAR-α coding region, spanning codons 40 to 54. Filters were washed in 2×SSC/0.1% SDS at room temperature twice for 20 minutes and exposed for 2 days to Kodak XAR-5 film with an intensifying screen at −80° C. Plaques corresponding to positive signals in duplicate were diluted in 10 mM Tris-HCl pH 7.5, 10 mM $MgCl_2$, replated on 90 mm plates, and re-screened as above. Phage DNA was prepared from positive plaques, digested with restriction enzymes and analysed by agarose gel electrophoresis followed by Southern blotting. The inserts of recombinant clones scored positive by Southern hybridization using MEO12 as the probe were subsequently cloned into Genescribe-Z vectors pTZ18 or pTZ19 (U.S. Biochemicals) for further sequence analyses. Four lambda clones, each containing inserts of at least 15 kb were isolated. FIG. 1A shows a restriction map for clone λ.91.1, a second partially overlapping clone λ.31.1, and plasmid subclones derived from them. A 1.2 kb Bam HI-Pst I region common to both genomic clones that hybridized to MEO12 (as determined by Southern blot analysis) was subcloned, giving the construct pBP31.1, and its DNA sequence was determined. A human cDNA library, constructed using polyA+ mRNA isolated from the human breast cancer cell line T47D [see, Petkovich, M. et al., Nature 330, 444–450 (1987)] was also screening using the oligonucleotide MEO12 and a clone, T2/20, was isolated from it. This randomly primed cDNA library was constructed from polyA+ mRNA obtained from the human breast cancer cell line T47-D and cloning was carried out as described previously [Petkovich, M. et al., Nature 330, 444–450 (1987)], except that the end-labelled oligonucleotide MEO12 was used as a hybridization probe. This clone, which contains a ≅800 bp insert, (FIG 2, in brackets) was sequenced.

It contains part of region B of hRAR-α, all of region A and an extensive 5'-untranslated region (5'-UTR) that is 541 bp long.

Comparison of the DNA sequence of the genomic subclone pBP31.1 (FIG. 1A) with that of the cDNA clone T2/20 revealed that the two sequences were identical upstream of the codon for $Thr_{60}$ over a distance of 540 bp (shown in upper case, Exon 2 in FIG. 2). At the 3' side, the genomic clone diverges from the T2/20 sequence within tile codon for $Thr_{60}$, where the DNA sequence reveals a potential splice donor site CCa/gtaagt (FIG. 2, intron sequence underlined and in lower case) resembling a consensus donor sequence $NAG/GTA_G{}^AGT$ [Shapiro, M. B. et al., Nucleic Acids Res. 15, 7155–7174 (1987)]. The isolation recently of cDNA clones for murine RAR-α, β and γ [Zelent, A. et al., Nature 339, 714–717 (1989); Kastner, P. et al., Proc. Natl. Acad. Sci. USA 87, 2700–2704 (1990)] and human RAR-γ [Krust, A. et al., Proc. Natl. Acad. Sci. USA 86, 5310–5314 (1989)] indicates that the boundary between regions A and B is sharply defined and well conserved. In hRAR-α, for example, the A/B boundary is located between Ala$_{59}$ and Thr$_{60}$, and correlates with previous observations [Petkovich, M. et al., Nature 330, 444–450 (1987); Brand, N. et al., Nature 332, 850–854 (1988); Dejean, A. et al., Nature 322, 70–72 (1986)] that this represents an exon boundary. Taken together, these data indicate that region A of hRAR-α (and 363 bp of the adjacent 5'-UTR) are encoded on a separate exon from that encoding region B, and strongly suggests that this boundary occurs at an equivalent position in the β and γ receptors.

The genomic and cDNA sequences diverged completely at a point located 176 bp downstream from the 5' end of T2/20 and approximately 500 bp from the 5' end of the pBP31.1 insert. In pBP31.1, this divergence from the cDNA sequence occurs at the first underlined portion of SEQ.ID.NO.:2 (FIG. 2) that resembles a splice acceptor stie [Shapiro, M. B. et al., Nucleic Acids Res. 15, 7155–7174 (1987)]. The identity of this splice site was confirmed by nuclease S1 mapping [Zenke, M. et al., EMBO J. 5, 387–397 (1986)] using a 600 nt single-stranded end-labelled probe, extended from an antisense oligonucleotide MQ300 which hybridizes within the 5'-UTR portion of the exon (see FIG. 1A and FIG. 2). A protected fragment of 277 nt in length was seen with MCF-7 or T47-D total RNA, but not with yeast tRNA. This result confirmed the length of the exon 2 contained within pBP31.1 as being 540 bp.

These data indicated that the first amino acid coding exon (exon 2 encoding region A in FIG. 2) was preceded by at least one upstream exon. To isolate this exon, a 190 bp Eco RI-Bst II fragment from the extreme 5' end of T2/20 was end-labelled and used to isolate a 1.1 kb Sal I-Eco RI fragment of the genomic clone lambda γ91.1. The fragment was cloned, giving the recombinant pRS7, and its DNA sequence was determined. The sequence revealed that this fragment indeed contained the 178 bp from the 5' end of T2/20 as a contiguous sequence, thus encoded in a single exon (see FIG. 2, exon 1). A putative splice donor site GAG/gtaatt (see above) (underlined in FIG. 2, intron sequence in lower case) was identified at the 3' side of this DNA sequence. In the genomic clone lambda γ91.1, this 5'-UTR sequence encoded in exon 1 and present in the cDNA clone T2/20, is separated from exon 2 by an intron which, by mapping and Southern blotting, is at least 12 kb in length, and is preceded by a sequence of 535 bp (FIG. 2). It should be noted that the cDNA clone T2/20 is co-linear with the hRAR-α cDNA sequences reported by Petkovich, M. et al., Nature 330, 444–450 (1987) and Giguere et al., Nature 330, 624–629 (1987), but extends it in the 5' direction by 573 bp and 438 bp, respectively.

EXAMPLE 2
Identification of the hRAR-α promoter

The 5' boundary of exon 1 contained within the genomic subclone pRS7 was determined by nuclease S1 mapping and primer extension analysis. A 614 nt-long [$^{32}$p]-end-labelled S1 nuclease probe, extended from the oligonucleotide MQ9 that is complementary to a sequence in hRAR-α exon 1 (FIG. 2), protected a major fragment of ≈80 nt length following hybridization to MCF-7 or T47D polyA+ mRNA and nuclease S1 digestion. Primer extension from the oligonucleotide MQ9 hybridized to MCF-7 or T47-D polyA+ mRNA generated an extended fragment of approximately the same size. These results suggested that the cDNA clone T2/20 contained the entire hRAR-α 5'-UTR.

Figure 1B:
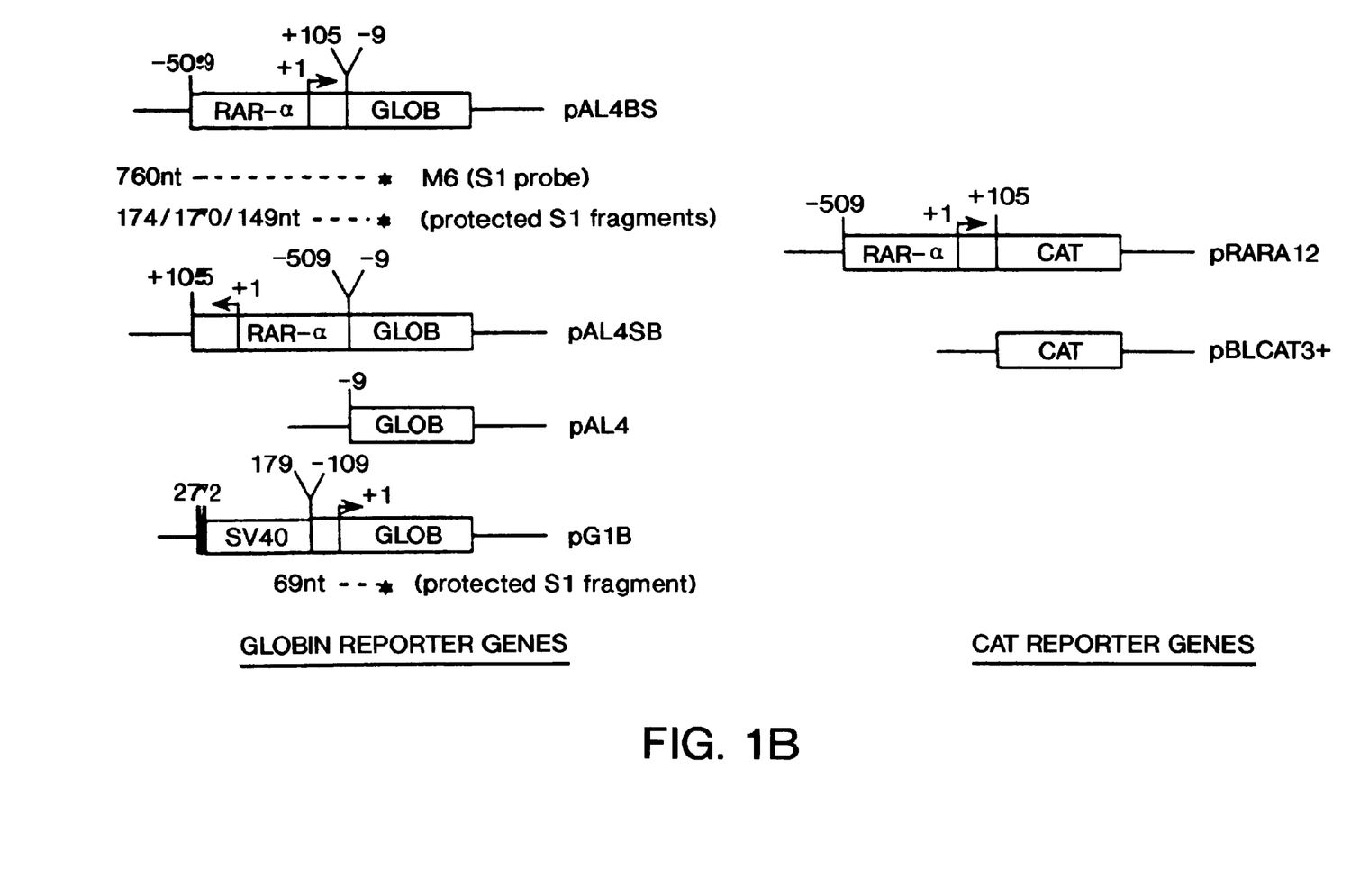

To address the possibility that the genomic fragment contained in pRS7 might in fact contain the hRAR-α promoter, HeLa cells were transfected with constructs in which the 614 bp 5' Bam HI-Sma I fragment of the genomic subclone pRS7 (see FIG 1a and 2) containing part of hRAR-α exon 1 and sequences upstream, was inserted upstream of rabbit β-globin coding sequences in the vector pAL4 (see FIG. 1B). This fragment was cloned into the polylinker of pAL4 in either the natural or reverse orientations, giving the constructs pAL4BS and pAL4SB, respectively (FIG. 1B). 10 μg of either a construct containing the Bam HI-Sma I fragment inserted in the natural orientation (pAL4BS), the reverse orientation (pAL4SB) or the promoterless parent vector (pAL4) were transfected into HeLa cells in culture, together with 400 ng of a β-globin reference plasmid pG1B [Wasylyk, C. et al., EMBO J. 5 553–560 (1986)], containing the rabbit β-globin promoter from −109 and downstream coding sequences (see FIG. 1B), and carrier DNA (Bluescribe 13+ BSM+) to a final concentration of 20 μg. Transfections were carried out as described previously [Petkovich, M. et al., Nature 330, 444–450 (1987)]. After 48 hours, cytoplasmic RNA was prepared from transfected dishes using standard procedures [Gough, N. M., Anal. Biochem. 173, 93–95 (1988)].

A 760 nt [$^{32}$P] 5' end-labelled single-stranded probe was generated by extending an oligonucleotide primer M6 a sequence, complementary to +39/+60 of the rabbit β-globin gene) annealed to a single-stranded template derived from pAL4BS (FIG. 1B). The probe was purified by gel electrophoresis and hybridized to RNA prepared from cells transfected as described above. S1 nuclease mapping was performed as described previously [Zenke, M. et al., EMBO J. 5, 387–397 (1986)]. The purified probe protects a fragment of 69 nt from the internal control plasmid pG1B. S1 nuclease digestion products were resolved on 6% acrylamide gels alongside dideoxy sequencing ladders primed with the oligonucleotide M6. Following autoradiography, all samples were reloaded on a second gel so as to normalize loading with respect to the pG1B signal. Cytoplasmic RNA, prepared from HeLa cells transfected with either of these constructs or the parental vector, was hybridized to a labelled single-stranded DNA probe spanning the Bam HI-Sma I fragment and part of exon 1 of the β-globin gene (FIG. 1B; M6 probe), and subjected to nuclease S1 mapping.

Figure 3:
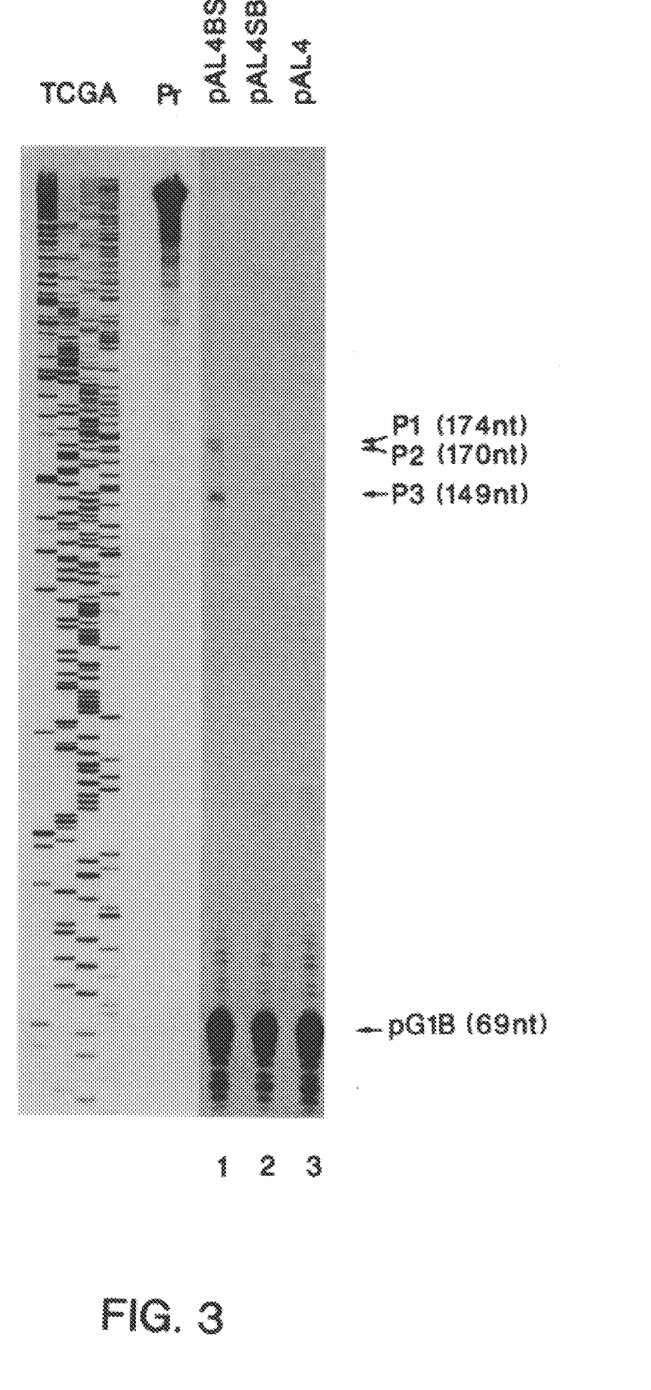

The results, normalized with respect to a cotransfected reference β-globin-containing plasmid, pG1B [Wasylyk, C. et al., EMBO J. 5, 553–560 (1986)], are shown in FIG. 3. Three major start-sites of transcription, designated P1, P2 and P3, with P1 being the most 5' of the three and therefore corresponding to the start of exon 1 for the hRAR-α gene (FIG. 2, +1), were detected in pAL4BS-trasfections, giving nuclease S1 -protected fragments of 174, 170 and 149 nt in length, respectively (FIG. 3, lane 1). Conversely, in pAL4SB, where the genomic Bam HI-Sma I fragment was inserted in the reverse orientation, there was no detectable transcription (FIG. 3, lane 2), nor was transcription detected with the parental vector pAL4 (lane 3). The cotransfected control plasmid pG1B was expressed in all cases, as shown by the presence of the expected 69 nt protected fragment (see FIG. 3, lanes 1 to 3). pG1B contains one copy of the 72 bp repeat from the SV40 enhancer linked immediately upstream to the β-globin promoter, which accounts for the high level of expression seen with 400 ng of pG1B transfected when compared with 10 μg of the hRAR-β promoter construct cotransfected, and supports previous observations that hRAR-β RNA is expressed at a low level [Petkovich, M. et al., Nature 330, 444–450 (1987)]. Identical results were obtained when Cos-1 cells were transfected with the same constructs (data not shown). Taken together, these data indicate that the Bam HI Sma I fragment contains a promoter region that functions in HeLa and Cos-1 cells, when cis-linked to a β-globin reporter gene.

By comparison to a DNA sequence ladder, all three transcription start-sites P1, P2 and P3 (FIG. 2., bold underlines) map in the vicinity of the 5' end of the cDNA clone T2/20 as indicated in FIG. 2. hRAR-α exon 1 is therefore ≅204 bp long (FIG. 1A and FIG. 2). Note that P3 is located immediately 5' to the beginning of the T2/20 cDNA clone in agreement with the results of nuclease S1 mapping and primer extension analyses for the endogenous hRAR-α gene and its transcript (see above), suggesting that this clone contains full 5' cDNA sequences for a transcript that initiated at P3.

Inspection of the hRAR-α promoter sequence reveals that it lacks obvious TATA or CCAAT box sequences upstream of the P1–P3 transcriptional start-sites (FIG. 2). A sequence TTC$\underline{A}$GTCT located around start-site P1 resembles a consensus sequence CTC$\underline{A}$NTCT (where N equals any nucleotide, presumptive first nucleotide of the transcript underlined), recently proposed as a core initiator sequence for promoters transcribed by RNA polymerase B (II) which lack a TATA-box [Smale, S. T. et al., Cell 57, 103–113 (1989); Smale, S. T. et al., Proc. Natl. Acad. Sci. USA 87, 4509–4513 (1990)]. An equivalent sequence TTC$\underline{A}$GCCT surrounding P3 also resemble the consensus, but P2 (GTCTGGGG) shows little similarity. It is possible that the "P2" protected fragment is, in fact, a clipped form of the "P1" fragment, resulting from over-digestion by S1 nuclease. The hRAR-α first exon and 5' flanking sequences are extremely GC-rich and there are a number of sequences which resemble binding sites for the transcription factor Sp1, variants upon the consensus recognition sequences 5'-$_T^G$GGGCGG$_{AAT}^{GGC}$-3' (SEQ.ID.NO.:10) [Dynan, W. S. et al., Nature 319, 246–248 (1986)]. Five such sites, three in one orientation, two in the other, are located from –117 to –4, and show 8 or 9 out of 10 matches with the consensus (see FIG. 2; boxed sequences, orientation denoted by arrows). The most distal of the Sp1-like sequences overlaps with a sequence 5'-GCGGGGGCGG-3' (SEQ. ID. NO.:11) at –120 to –111, denoted in FIG. 2 by a dotted overline. This sequence matches exactly a binding site reported recently for the transcription factors Krox-20 and Krox-24 [Chavrier, P. et al, EMBO J. 9, 1209–1218 (1990); Lemaire, P. et al., Mol. Cell. Biol. 10, 3456–3467 (1990)]. Krox-20 protein was shown to bind in vitro to such a sequence located in the promoter of the mouse homeogene Hox-1.4. The site to which Krox-20 bound also overlapped with a sequence that was demonstrated to bind Sp1 [Chavrier, P. et al, EMBO J. 9, 1209–1218 (1990); Lemaire, P. et al., Mol. Cell. Biol. 10, 3456–3467 (1990)].

The 5' flanking region of the hRAR-α gene contains a number of other short sequences bearing homologies to DNA elements thought or shown, in particular instances, to bind transacting protein factors. A sequence 5'-AGGTGTGGGTG-3' (SEQ. ID. NO.:12) beginning at –347 (underlined, FIG. 2), resembles the GT-I motif of the SV40 enhancer, known to bind the HeLa cell enhancer factor TEF-2 [Davidson, I. et al., Cell 54, 931–942 (1988)]. In addition, there are two copies of a sequence 5'-GGAAGTG-3', (overlined in FIG. 2, orienation denoted by arrows), beginning at positions –496 on the sense strand, and at position –378 on the anti-sense strand, very similar (6 matches out of 7) to the recognition sequence for the protein factor E4TF1 that binds to the Adenovirus E4 promoter [Jones, N. C. et al., Genes & Development 2, 267–281 (1988)]. We note also that there are two copies of a sequence 5'-ATTATA-3' arranged in tandem in a short AT-rich region from –439 to –483. Interestingly, two copies of the sequence 5'-GGTCA-3' are seen at positions –485 and –479, identical to half-palindromic oestrogen/thryoid hormone/retinoic acid response elements [Umesono, K. et al., Nature 336, 262–265 (1988)] This tandem arrangement is also similar to a tandem repeat of the sequence 5'-GTTCAC-3' recently reported as a retinoic acid response element (RARE) for the human RAR-β promoter [de The, H. et al., Nature 343, 177–180 (1990)]. It was therefore investigated whether the hRAR-α promoter might be hormone-responsive.

EXAMPLE 3

Activity of the hRAR-α promoter in cultured cells

FIG. 4 shows the results of testing the hRAR-α promoter in a variety of cell lines by linking it to the chloramphenicol acetyl transferase (CAT) gene from E. coli. The vector pBLCAT3+ contains the bacterial CAT gene positioned upstream of SV40 polyadenylation signals [Luckow, B. et al., Nucleic Acids Res. 15, 5490 (1987)]. The 614 bp Bam HI-Sma I fragment of pRS7 was cloned into pBLCAT3+ that had been cut first with Bgl II, the ends made blunt by filling in with all four dNTPs and the Klenow fragment of DNA pol I, and then cut with Bam HI. The resulting recombinant pRARA12 (FIG. 1B), contains the RAR-α promoter fragment linked 5' to the CAT gene. Typically, 2–4 μg of the recombinant or the parent vector were used to transfect cells along with 2 μg of an internal standard plasmid pCH110 (Pharmacia), in which the bacterial lac-Z gene encoding β-galactosidase is under the control of the SV40 promoter. Carrier DNA was added to a final total of 20 μg. Other plasmids transfected were the chimaeric expression plasmid RAR-β.ER.CAS, encoding a chimaeric receptor in which the DNA binding domain of hRAR-β has been replaced by the corresponding region of the human oestrogen receptor [Brand, N. et al., Nature 332, 850–854 (1988)], the oestrogen-responsive reporter plasmid vit-tk-CAT and pSVCAT, in which the SV40 early promoter drives CAT expression. Transfections, culture and CAT assays were carried out as described previously [see, Petkovich, M. et al., Nature 330, 444–450 (1987)]. Where appropriate, hormones were added 20 hours after transfection to $10^{-8}$M final concentration (MCF-7, T47D) or $10^{-7}$M (all other cell lines). Control plates were treated with an equal volume of vehicle (ethanol). All transfections were carried out in duplicate. HeLa cells were grown in Dulbeccos modified medium supplemented with 5% stripped foetal calf serum (FCS); the human breast cancer: line MCF-7 was cultured with 10% FCS and 0.6 μg/ml insulin. The murine teratocarcinoma P19.6 was grown in Dulbeccos with 10% FCS. A second human breast cancer cell line used, T47D, was grown in RPMI containing 10% FCS and 0.6 μg/ml insulin but for transfection, the media was replaced with MCF-7 media for 4 hours prior to and for 20 hours following transfection. Either pBLCAT3+ or pRARA12 were transfected into a variety of cultured cell lines and, after 48 hours, crude cell lysates were prepared and assayed for CAT activity using previously described methods [Petkovich, M., et al., Nature 330, 444–450 (1987)]. FIG. 4A and B shows the result of transfecting increasing amounts of either CAT construct into HeLa cells. In accordance with the above (example 2) results obtained using the β-globin reporter plasmid, the promoterless vector pBLCAT3+ was inactive, whereas pRARA12 CAT expression was clearly driven by the –509/+105 [SEQ. ID NO. 1] region of the hRAR-α promoter. When the amount of pRARA12 DNA transfected per dish was increased from 1 to 10 μg (FIG. 4A, lanes 1 through 4), there was a corresponding increase in the amount of CAT activity observed; parallel transfections with the parental vector yielded no visible CAT activity (lanes 5 to 8). CAT activity reached a plateau level at ≅5 µg of pRARA12 transfected (FIG. 4A and B). Accordingly, between 2–4 µg of either pRATA12 or pBL3CAT+ were used thereafter.

Figure 4A:
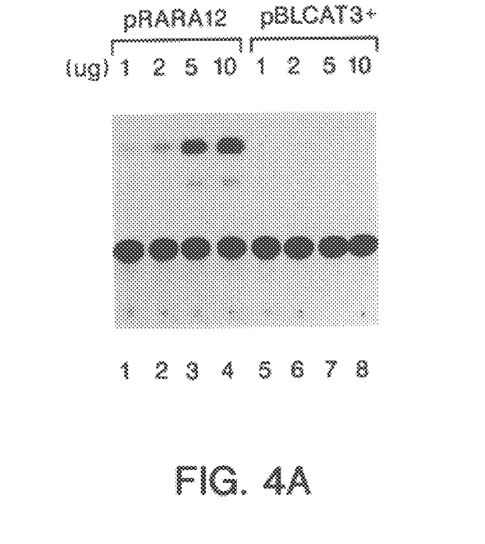
Figure 4B:
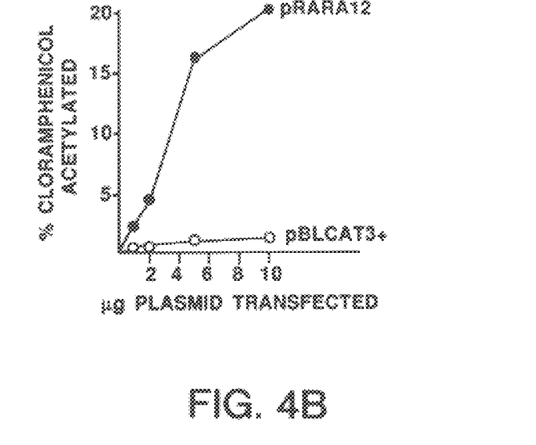
Figure 4C:
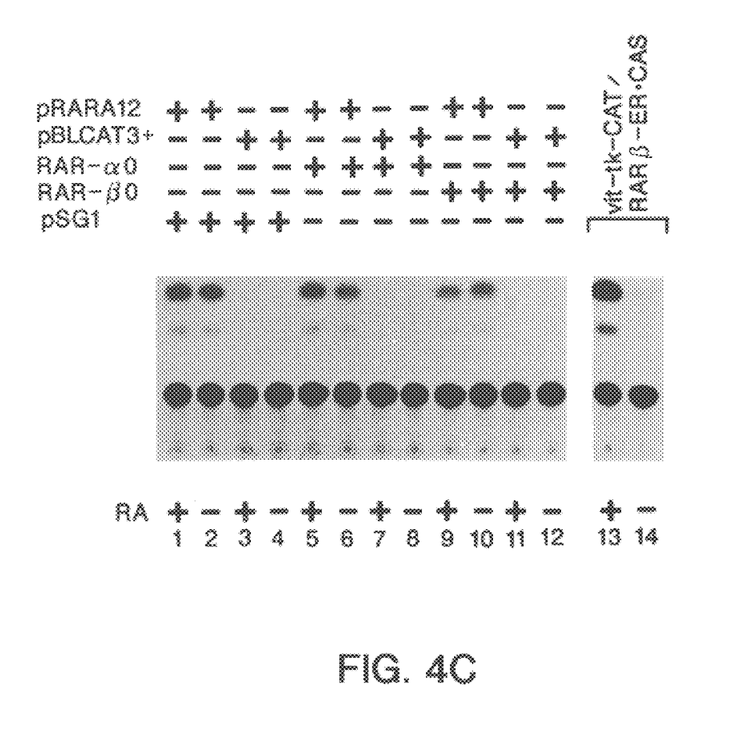

Also tested was whether RA, oestrogen or factors present in whole serum might regulate the activity of the hRAR-α promoter in HeLa cells. Treatment of HeLa cells in which the human oestrogen receptor (hER) expression vector HEO [Kumar, V., et al., Cell 51, 941–951 (1987)] was cotransfected with either pRARA12 or pBLCAT3+ and then cultured with hormone-stripped medium supplemented with 20 mM oestradiol (E2) did not alter CAT expression from pRARA12 (data not shown). HeLa cells were also cotransfected with 2 µg of pRARA12 and 2 µg of either the wild-type hRAR-α expression vector RAR-αφ or the wild-type hRAR-β expression vector RAR-βφ [Brand, N. et al., Nature 332, 850–854 (1988)]. The transfected cells were subsequently treated with $10^{-7}$M RA or vehicle (ethanol) as described above. FIG. 4C represents the results of a typical experiment. The slight variability between the signals seen for RA versus vehicle-treated cells (for example, compare lanes 9 and 10) was not significant, as judge from several independent experiments. As a RA positive control, the plasmid RAR-β.ER.CAS [Brand, N. et al., Nature 332, 850–854 (1988)], expressing a chimaeric receptor in which the putative DNA binding domain of RAR-β (domain C) has been replaced by the equivalent region from the hER, was used to trans-activate the ER-responsive plasmid vit-tk-CAT in the presence or absence of RA (FIG. 4C, compare lanes 13 and 14). HeLa cells were also treated with 15% whole (i.e. not stripped) serum for 24 hours following transfection. This also had no effect upon the level of CAT activity in pRARA12 transfections.

Figure 4D:
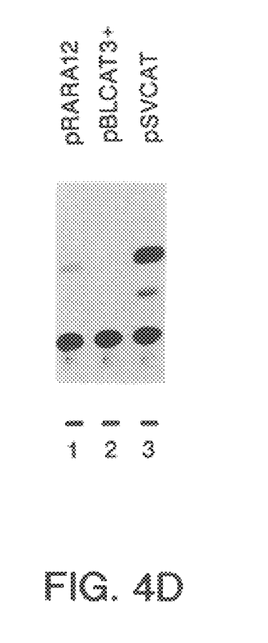

A variety of other cell types were transfected with pRARA12 or pBLCAT3+. Some murine embryonal carcinoma (EC) cells such as the F9 and P19 lines are responsive, to RA, undergoing terminal differentiation when treated with nano- or micromolar concentrations of RA [for example, see Strickland, S. et al., Cell 15, 393–403 (1978); Sharma, S. et al., Developmental Biology 125, 246–254 (1988); Jones-Villeneuve, E. M. V. et al., J. Cell Biol. 94, 253–262 (1982)]. Weak expression of pRATA12 was seen in transfected P19.6 cells, with no visible activity from the promoterless pBLCAT3+ (FIG. 4D, compare lanes 1 and 2). The SV40-driven reporter pSV-CAT was also transfected and was strongly expressed in P19.6 cells (FIG. 4D, lane 3). pSV-CAT was also expressed strongly in the human breast cancer cells lines MCF-7 and T47D, but no CAT activity was observed when these lines were transfected with pRARA12 (data not shown). This was a surprising result given that hRAR-α is expressed in MCF-7 and T47D cell lines [Petkovich, M. et al., Nature 330, 444–450 (1987)]. The hRAR-α promoter may be positively regulated by trans-acting factors present in T47D and MCF-7 cells that bind to some far upstream element not represented in the pRAR12 clone.

All publications and patents referred to in the present application are incorporated herein by reference to the same extent as if each individual publication or patent was specifically and individually indicated to be incorporated by reference.

What is claimed is:

1. An isolated DNA sequence consisting of a human retinoic acid receptor α (hRAR-α) gene promoter.

2. The isolated DNA sequence according to claim 1 which is the nucleotide sequence of −509 to +105 as shown in FIG. 2.

3. An isolated DNA sequence comprising a heterologous gene operatively linked to a human retinoic acid receptor α (hRAR-α) gene promoter.

4. The isolated DNA sequence according to claim 3, wherein the human retinoic acid receptor α (hRAR-α) gene promoter is the nucleotide sequence of −509 to +105 as shown in FIG. 2.

5. The isolated DNA sequence according to claims 3 or 4, wherein the heterologous gene is the chloramphenicol acetyl transferase gene from *Escherichia coli*.

6. An expression vector comprising a promoter, wherein the promoter consists of a human retinoic acid receptor α (hRAR-α) gene promoter.

7. The expression vector according to claim 6, wherein the hRAR-α gene promoter is the nucleotide sequence of −509 to +105 as shown in FIG. 2.

8. The expression vector according to claims 6 or 7, further comprising a heterologous gene operatively linked to the hRAR-α gene promoter.

9. The expression vector according to claim 8, wherein the heterologous gene is the chloramphenicol acetyl transferase gene from *Escherichia coli*.

10. A host cell containing the expression vector according to claims 6 or 7.

11. A host cell containing the expression vector according to claim 8.

12. A host cell containing the expression vector according to claim 9.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 614 base pairs
        (B) TYPE: nucleic acid
        (C) STRANDEDNESS: double
        (D) TOPOLOGY: linear     (ii) MOLECULE TYPE: DNA (genomic)

(ix) FEATURE:
        (A) NAME/KEY: CDS
        (B) LOCATION: 556..582

(xi) SEQUENCE DESCRIPTION: SEQ ID NO:1:

```
GGATCCAGGG AAGGGAAGTG ACTTGGTCAA GGTCACACAG CTCTCAGTTC CAGCTGGTCC      60

CTAGAAGAGG ATTATAATTA TAGGATTCAG GGGCTTGACA GCTAGGGCCA GGAGTCACCG     120

CCATCACTTC CATATTACGC CGCCGCCTCA CTTCTCAGAT TTAGGTGTGG GTGTGTGTGT     180

GGTTGGGGGG AAAGGAGTGT AGGATACCAC ACGCTGCGGT CTTCTCCACC GAGCGCTATT     240

TTCATTCTTT CCGCAGAACC TCACCCCGTT CTTGCTCTGA ATCTTCGGTT CTGGGTCTGA     300

GGGAGGGATT CTCCCGGATT CCCACGGTCC AGTCTTCAAC TAGGAGTGGC TCCTTTAAGA     360

CTCGCCCTTC CCAGGTCTAT TAAGGAGAGG CGGGGCGGG CGTGAGCCTG TAGATCCGCC      420

CCTGACTGGT GATTGGTCGG TGGGCGGGCA GGGGCGGGCC TGAGGGACAG GGCCTCCCCC     480
```

```
                                                              -continued

TACCTCTGCT CCGTACCCTC CGCCCCTTCA GTCTGGGGCT CCGGGTAAAG TTTCAGCCTC    540

CGCACGTGAC TCGCT ATG GCC GCT GCC ATC GCC CCG CGC CCC TGAGCCGCGG     592
              Met Ala Ala Ala Ile Ala Pro Arg Pro
                1               5

CCCCCTGGAC GGCTCCTCTC CC                                            614

(2) INFORMATION FOR SEQ ID NO:2:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ala Ala Ile Ala Pro Arg Pro
  1               5
```